(12) United States Patent
Layman

(10) Patent No.: US 8,906,316 B2
(45) Date of Patent: Dec. 9, 2014

(54) FLUID RECIRCULATION SYSTEM FOR USE IN VAPOR PHASE PARTICLE PRODUCTION SYSTEM

(71) Applicant: SDCmaterials, Inc., Tempe, AZ (US)

(72) Inventor: Frederick P. Layman, Carefree, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 0 days.

(21) Appl. No.: 13/907,667

(22) Filed: May 31, 2013

(65) Prior Publication Data

US 2014/0151939 A1    Jun. 5, 2014

Related U.S. Application Data

(63) Continuation of application No. 12/151,765, filed on May 8, 2008, now Pat. No. 8,574,408.

(60) Provisional application No. 60/928,946, filed on May 11, 2007.

(51) Int. Cl.
*B01J 19/08* (2006.01)
*B22F 9/12* (2006.01)

(52) U.S. Cl.
USPC ........................................ 422/186.04; 75/346

(58) Field of Classification Search
USPC ........................................ 422/186.04; 75/346
See application file for complete search history.

(56) References Cited

U.S. PATENT DOCUMENTS

| | | | |
|---|---|---|---|
| 2,021,936 A | 11/1935 | Johnstone | |
| 2,284,554 A | 5/1942 | Beyerstedt | |
| 2,419,042 A | 4/1947 | Todd | |
| 2,519,531 A | 8/1950 | Worn | |
| 2,562,753 A | 7/1951 | Trost | |
| 2,689,780 A | 9/1954 | Rice | |
| 3,001,402 A | 9/1961 | Koblin | |
| 3,042,511 A | 7/1962 | Reding, Jr. | |

(Continued)

FOREIGN PATENT DOCUMENTS

| | | |
|---|---|---|
| DE | 34 45 273 A1 | 6/1986 |
| EP | 1 134 302 A1 | 9/2001 |

(Continued)

OTHER PUBLICATIONS

Bateman, J. E. et al. (Dec. 17, 1998). "Alkylation of Porous Silicon by Direct Reaction with Alkenes and Alkynes," *Angew. Chem Int. Ed.* 37(19):2683-2685.

(Continued)

*Primary Examiner* — Kishor Mayekar
(74) *Attorney, Agent, or Firm* — Morrison & Foerster LLP

(57) ABSTRACT

A method of and system for recirculating a fluid in a particle production system. A reactor produces a reactive particle-gas mixture. A quench chamber mixes a conditioning fluid with the reactive particle-gas mixture, producing a cooled particle-gas mixture that comprises a plurality of precursor material particles and an output fluid. A filter element filters the output fluid, producing a filtered output. A temperature control module controls the temperature of the filtered output, producing a temperature-controlled, filtered output. A content ratio control module modulates the content of the temperature-controlled, filtered output, thereby producing a content-controlled, temperature-controlled, filtered output. A channeling element supplies the content-controlled, temperature-controlled, filtered output to the quench chamber, wherein the content-controlled, filtered output is provided to the quench chamber as the conditioning fluid to be used in cooling the reactive particle-gas mixture.

20 Claims, 4 Drawing Sheets

(56) References Cited

U.S. PATENT DOCUMENTS

| | | |
|---|---|---|
| 3,067,025 A | 12/1962 | Chisholm |
| 3,145,287 A | 8/1964 | Siebein et al. |
| 3,178,121 A | 4/1965 | Wallace, Jr. |
| 3,179,782 A | 4/1965 | Matvay |
| 3,181,947 A | 5/1965 | Vordahl |
| 3,313,908 A | 4/1967 | Unger et al. |
| 3,401,465 A | 9/1968 | Larwill |
| 3,450,926 A | 6/1969 | Kiernan |
| 3,457,788 A | 7/1969 | Nobuo Miyajima |
| 3,537,513 A | 11/1970 | Austin |
| 3,552,653 A | 1/1971 | Inoue |
| 3,617,358 A | 11/1971 | Dittrich |
| 3,667,111 A | 6/1972 | Chartet |
| 3,741,001 A | 6/1973 | Fletcher et al. |
| 3,752,172 A | 8/1973 | Cohen et al. |
| 3,761,360 A | 9/1973 | Auvil et al. |
| 3,774,442 A | 11/1973 | Gustaysson |
| 3,804,034 A | 4/1974 | Stiglich, Jr. |
| 3,830,756 A | 8/1974 | Sanchez et al. |
| 3,871,448 A | 3/1975 | Vann et al. |
| 3,892,882 A | 7/1975 | Guest et al. |
| 3,914,573 A | 10/1975 | Muehlberger |
| 3,959,094 A | 5/1976 | Steinberg |
| 3,959,420 A | 5/1976 | Geddes et al. |
| 3,969,482 A | 7/1976 | Teller |
| 4,008,620 A | 2/1977 | Narato et al. |
| 4,018,388 A | 4/1977 | Andrews |
| 4,021,021 A | 5/1977 | Hall et al. |
| 4,127,760 A | 11/1978 | Meyer et al. |
| 4,139,497 A | 2/1979 | Castor et al. |
| 4,157,316 A | 6/1979 | Thompson et al. |
| 4,171,288 A | 10/1979 | Keith et al. |
| 4,174,298 A | 11/1979 | Antos |
| 4,189,925 A | 2/1980 | Long |
| 4,227,928 A | 10/1980 | Wang |
| 4,248,387 A | 2/1981 | Andrews |
| 4,253,917 A | 3/1981 | Wang |
| 4,260,649 A | 4/1981 | Dension et al. |
| 4,284,609 A | 8/1981 | deVries |
| 4,315,874 A | 2/1982 | Ushida et al. |
| 4,326,492 A | 4/1982 | Leibrand, Sr. et al. |
| 4,344,779 A | 8/1982 | Isserlis |
| 4,369,167 A | 1/1983 | Weir |
| 4,388,274 A | 6/1983 | Rourke et al. |
| 4,419,331 A | 12/1983 | Montalvo |
| 4,431,750 A | 2/1984 | McGinnis et al. |
| 4,436,075 A | 3/1984 | Campbell et al. |
| 4,440,733 A | 4/1984 | Lawson et al. |
| 4,458,138 A | 7/1984 | Adrian et al. |
| 4,459,327 A | 7/1984 | Wang |
| 4,505,945 A | 3/1985 | Dubust et al. |
| 4,513,149 A | 4/1985 | Gray et al. |
| 4,523,981 A | 6/1985 | Ang et al. |
| 4,545,872 A | 10/1985 | Sammells et al. |
| RE32,244 E | 9/1986 | Andersen |
| 4,609,441 A | 9/1986 | Frese, Jr. et al. |
| 4,723,589 A | 2/1988 | Iyer et al. |
| 4,731,517 A | 3/1988 | Cheney |
| 4,751,021 A | 6/1988 | Mollon et al. |
| 4,764,283 A | 8/1988 | Ashbrook et al. |
| 4,765,805 A | 8/1988 | Wahl et al. |
| 4,824,624 A | 4/1989 | Palicka et al. |
| 4,836,084 A | 6/1989 | Vogelesang et al. |
| 4,855,505 A | 8/1989 | Koll |
| 4,866,240 A | 9/1989 | Webber |
| 4,885,038 A | 12/1989 | Anderson et al. |
| 4,921,586 A | 5/1990 | Molter |
| 4,983,555 A | 1/1991 | Roy et al. |
| 4,987,033 A | 1/1991 | Abkowitz et al. |
| 5,006,163 A | 4/1991 | Benn et al. |
| 5,015,863 A | 5/1991 | Takeshima et al. |
| 5,041,713 A | 8/1991 | Weidman |
| 5,043,548 A | 8/1991 | Whitney et al. |
| 5,070,064 A | 12/1991 | Hsu et al. |
| 5,073,193 A | 12/1991 | Chaklader et al. |
| 5,133,190 A | 7/1992 | Abdelmalek |
| 5,151,296 A | 9/1992 | Tokunaga |
| 5,157,007 A | 10/1992 | Domesle et al. |
| 5,192,130 A | 3/1993 | Endo et al. |
| 5,230,844 A | 7/1993 | Macaire et al. |
| 5,233,153 A | 8/1993 | Coats |
| 5,269,848 A | 12/1993 | Nakagawa |
| 5,330,945 A | 7/1994 | Beckmeyer et al. |
| 5,338,716 A | 8/1994 | Triplett et al. |
| 5,369,241 A | 11/1994 | Taylor et al. |
| 5,371,049 A | 12/1994 | Moffett et al. |
| 5,372,629 A | 12/1994 | Anderson et al. |
| 5,392,797 A | 2/1995 | Welch |
| 5,436,080 A | 7/1995 | Inoue et al. |
| 5,439,865 A | 8/1995 | Abe et al. |
| 5,442,153 A | 8/1995 | Marantz et al. |
| 5,460,701 A | 10/1995 | Parker et al. |
| 5,464,458 A | 11/1995 | Yamamoto |
| 5,485,941 A | 1/1996 | Guyomard et al. |
| 5,534,149 A | 7/1996 | Birkenbeil et al. |
| 5,534,270 A | 7/1996 | De Castro |
| 5,543,173 A | 8/1996 | Horn, Jr. et al. |
| 5,553,507 A | 9/1996 | Basch et al. |
| 5,562,966 A | 10/1996 | Clarke et al. |
| 5,582,807 A | 12/1996 | Liao et al. |
| 5,596,973 A | 1/1997 | Grice |
| 5,611,896 A | 3/1997 | Swanepoel et al. |
| 5,630,322 A | 5/1997 | Heilmann et al. |
| 5,652,304 A | 7/1997 | Calderon et al. |
| 5,714,644 A | 2/1998 | Irgang et al. |
| 5,723,187 A | 3/1998 | Popoola et al. |
| 5,726,414 A | 3/1998 | Kitahashi et al. |
| 5,749,938 A | 5/1998 | Coombs |
| 5,776,359 A | 7/1998 | Schultz et al. |
| 5,788,738 A | 8/1998 | Pirzada et al. |
| 5,804,155 A | 9/1998 | Farrauto et al. |
| 5,811,187 A | 9/1998 | Anderson et al. |
| 5,837,959 A | 11/1998 | Muehlberger et al. |
| 5,851,507 A | 12/1998 | Pirzada et al. |
| 5,853,815 A | 12/1998 | Muehlberger |
| 5,858,470 A | 1/1999 | Bernecki et al. |
| 5,884,473 A | 3/1999 | Noda et al. |
| 5,905,000 A | 5/1999 | Yadav et al. |
| 5,928,806 A | 7/1999 | Olah et al. |
| 5,935,293 A | 8/1999 | Detering et al. |
| 5,973,289 A | 10/1999 | Read et al. |
| 5,989,648 A | 11/1999 | Phillips |
| 5,993,967 A | 11/1999 | Brotzman, Jr. et al. |
| 5,993,988 A | 11/1999 | Ohara et al. |
| 6,004,620 A | 12/1999 | Camm |
| 6,012,647 A | 1/2000 | Ruta et al. |
| 6,033,781 A | 3/2000 | Brotzman, Jr. et al. |
| 6,045,765 A | 4/2000 | Nakatsuji et al. |
| 6,059,853 A | 5/2000 | Coombs |
| 6,066,587 A | 5/2000 | Kurokawa et al. |
| 6,084,197 A | 7/2000 | Fusaro, Jr. |
| 6,093,306 A | 7/2000 | Hanrahan et al. |
| 6,093,378 A | 7/2000 | Deeba et al. |
| 6,102,106 A | 8/2000 | Manning et al. |
| 6,117,376 A | 9/2000 | Merkel |
| 6,168,694 B1 | 1/2001 | Huang et al. |
| 6,190,627 B1 | 2/2001 | Hoke et al. |
| 6,213,049 B1 | 4/2001 | Yang |
| 6,214,195 B1 | 4/2001 | Yadav et al. |
| 6,228,904 B1 | 5/2001 | Yadav et al. |
| 6,254,940 B1 | 7/2001 | Pratsinis et al. |
| 6,261,484 B1 | 7/2001 | Phillips et al. |
| 6,267,864 B1 | 7/2001 | Yadav et al. |
| 6,322,756 B1 | 11/2001 | Arno et al. |
| 6,342,465 B1 | 1/2002 | Klein et al. |
| 6,344,271 B1 | 2/2002 | Yadav et al. |
| 6,362,449 B1 | 3/2002 | Hadidi et al. |
| 6,379,419 B1 | 4/2002 | Celik et al. |
| 6,387,560 B1 | 5/2002 | Yadav et al. |
| 6,395,214 B1 | 5/2002 | Kear et al. |
| 6,398,843 B1 | 6/2002 | Tarrant |
| 6,399,030 B1 | 6/2002 | Nolan |
| 6,409,851 B1 | 6/2002 | Sethuram et al. |
| 6,413,781 B1 | 7/2002 | Geis et al. |

(56) References Cited

U.S. PATENT DOCUMENTS

| | | |
|---|---|---|
| 6,416,818 B1 | 7/2002 | Aikens et al. |
| RE37,853 E | 9/2002 | Detering et al. |
| 6,444,009 B1 | 9/2002 | Liu et al. |
| 6,475,951 B1 | 11/2002 | Domesle et al. |
| 6,488,904 B1 | 12/2002 | Cox et al. |
| 6,506,995 B1 | 1/2003 | Fusaro, Jr. et al. |
| 6,517,800 B1 | 2/2003 | Cheng et al. |
| 6,524,662 B2 | 2/2003 | Jang et al. |
| 6,531,704 B2 | 3/2003 | Yadav et al. |
| 6,548,445 B1 | 4/2003 | Buysch et al. |
| 6,554,609 B2 | 4/2003 | Yadav et al. |
| 6,562,304 B1 | 5/2003 | Mizrahi |
| 6,562,495 B2 | 5/2003 | Yadav et al. |
| 6,569,393 B1 | 5/2003 | Hoke et al. |
| 6,569,397 B1 | 5/2003 | Yadav et al. |
| 6,569,518 B2 | 5/2003 | Yadav et al. |
| 6,572,672 B2 | 6/2003 | Yadav et al. |
| 6,579,446 B1 | 6/2003 | Teran et al. |
| 6,596,187 B2 | 7/2003 | Coll et al. |
| 6,603,038 B1 | 8/2003 | Hagemeyer et al. |
| 6,607,821 B2 | 8/2003 | Yadav et al. |
| 6,610,355 B2 | 8/2003 | Yadav et al. |
| 6,623,559 B2 | 9/2003 | Huang |
| 6,635,357 B2 | 10/2003 | Moxson et al. |
| 6,641,775 B2 | 11/2003 | Vigliotti et al. |
| 6,652,822 B2 | 11/2003 | Phillips et al. |
| 6,652,967 B2 | 11/2003 | Yadav et al. |
| 6,669,823 B1 | 12/2003 | Sarkas et al. |
| 6,682,002 B2 | 1/2004 | Kyotani |
| 6,689,192 B1 | 2/2004 | Phillips et al. |
| 6,699,398 B1 | 3/2004 | Kim |
| 6,706,097 B2 | 3/2004 | Zomes |
| 6,706,660 B2 | 3/2004 | Park |
| 6,710,207 B2 | 3/2004 | Bogan, Jr. et al. |
| 6,713,176 B2 | 3/2004 | Yadav et al. |
| 6,716,525 B1 | 4/2004 | Yadav et al. |
| 6,744,006 B2 | 6/2004 | Johnson et al. |
| 6,746,791 B2 | 6/2004 | Yadav et al. |
| 6,772,584 B2 | 8/2004 | Chun et al. |
| 6,786,950 B2 | 9/2004 | Yadav et al. |
| 6,813,931 B2 | 11/2004 | Yadav et al. |
| 6,817,388 B2 | 11/2004 | Tsangaris et al. |
| 6,832,735 B2 | 12/2004 | Yadav et al. |
| 6,838,072 B1 | 1/2005 | Kong et al. |
| 6,841,509 B1 | 1/2005 | Hwang et al. |
| 6,855,410 B2 | 2/2005 | Buckley |
| 6,855,426 B2 | 2/2005 | Yadav |
| 6,855,749 B1 | 2/2005 | Yadav et al. |
| 6,858,170 B2 | 2/2005 | Van Thillo et al. |
| 6,886,545 B1 | 5/2005 | Holm |
| 6,891,319 B2 | 5/2005 | Dean et al. |
| 6,896,958 B1 | 5/2005 | Cayton et al. |
| 6,902,699 B2 | 6/2005 | Fritzemeier et al. |
| 6,916,872 B2 | 7/2005 | Yadav et al. |
| 6,919,065 B2 | 7/2005 | Zhou et al. |
| 6,919,527 B2 | 7/2005 | Boulos et al. |
| 6,933,331 B2 | 8/2005 | Yadav et al. |
| 6,972,115 B1 | 12/2005 | Ballard |
| 6,986,877 B2 | 1/2006 | Takikawa et al. |
| 6,994,837 B2 | 2/2006 | Boulos et al. |
| 7,007,872 B2 | 3/2006 | Yadav et al. |
| 7,022,305 B2 | 4/2006 | Drumm et al. |
| 7,052,777 B2 | 5/2006 | Brotzman, Jr. et al. |
| 7,073,559 B2 | 7/2006 | O'Larey et al. |
| 7,074,364 B2 | 7/2006 | Jähn et al. |
| 7,081,267 B2 | 7/2006 | Yadav |
| 7,101,819 B2 | 9/2006 | Rosenflanz et al. |
| 7,147,544 B2 | 12/2006 | Rosenflanz |
| 7,147,894 B2 | 12/2006 | Zhou et al. |
| 7,166,198 B2 | 1/2007 | Van Der Walt et al. |
| 7,166,663 B2 | 1/2007 | Cayton et al. |
| 7,172,649 B2 | 2/2007 | Conrad et al. |
| 7,172,790 B2 | 2/2007 | Koulik et al. |
| 7,178,747 B2 | 2/2007 | Yadav et al. |
| 7,208,126 B2 | 4/2007 | Musick et al. |
| 7,211,236 B2 | 5/2007 | Stark et al. |
| 7,217,407 B2 | 5/2007 | Zhang |
| 7,220,398 B2 | 5/2007 | Sutorik et al. |
| 7,255,498 B2 | 8/2007 | Bush et al. |
| 7,265,076 B2 | 9/2007 | Taguchi et al. |
| 7,282,167 B2 | 10/2007 | Carpenter |
| 7,307,195 B2 | 12/2007 | Polverejan et al. |
| 7,323,655 B2 | 1/2008 | Kim |
| 7,384,447 B2 | 6/2008 | Kodas et al. |
| 7,402,899 B1 | 7/2008 | Whiting et al. |
| 7,417,008 B2 | 8/2008 | Richards et al. |
| 7,494,527 B2 | 2/2009 | Jurewicz et al. |
| 7,517,826 B2 | 4/2009 | Fujdala et al. |
| 7,534,738 B2 | 5/2009 | Fujdala et al. |
| 7,541,012 B2 | 6/2009 | Yeung et al. |
| 7,541,310 B2 | 6/2009 | Espinoza et al. |
| 7,557,324 B2 | 7/2009 | Nylen et al. |
| 7,572,315 B2 | 8/2009 | Boulos et al. |
| 7,576,029 B2 | 8/2009 | Saito et al. |
| 7,576,031 B2 | 8/2009 | Beutel et al. |
| 7,604,843 B1 | 10/2009 | Robinson et al. |
| 7,611,686 B2 | 11/2009 | Alekseeva et al. |
| 7,615,097 B2 | 11/2009 | McKeclutie et al. |
| 7,618,919 B2 | 11/2009 | Shimazu et al. |
| 7,622,693 B2 | 11/2009 | Foret |
| 7,632,775 B2 | 12/2009 | Zhou et al. |
| 7,635,218 B1 | 12/2009 | Lott |
| 7,674,744 B2 | 3/2010 | Shiratori et al. |
| 7,678,419 B2 | 3/2010 | Kevwitch et al. |
| 7,704,369 B2 | 4/2010 | Olah et al. |
| 7,709,411 B2 | 5/2010 | Zhou et al. |
| 7,709,414 B2 | 5/2010 | Fujdala et al. |
| 7,745,367 B2 | 6/2010 | Fujdala et al. |
| 7,750,265 B2 | 7/2010 | Belashchenko et al. |
| 7,803,210 B2 | 9/2010 | Sekine et al. |
| 7,842,515 B2 | 11/2010 | Zou et al. |
| 7,851,405 B2 | 12/2010 | Wakamatsu et al. |
| 7,874,239 B2 | 1/2011 | Howland |
| 7,875,573 B2 | 1/2011 | Beutel et al. |
| 7,897,127 B2 | 3/2011 | Layman et al. |
| 7,902,104 B2 | 3/2011 | Kalck |
| 7,905,942 B1 | 3/2011 | Layman |
| 7,935,655 B2 | 5/2011 | Tolmachev |
| 8,051,724 B1 | 11/2011 | Layman et al. |
| 8,076,258 B1 | 12/2011 | Biberger |
| 8,080,494 B2 | 12/2011 | Yasuda et al. |
| 8,089,495 B2 | 1/2012 | Keller |
| 8,142,619 B2 | 3/2012 | Layman et al. |
| 8,168,561 B2 | 5/2012 | Virkar |
| 8,173,572 B2 | 5/2012 | Feaviour |
| 8,211,392 B2 | 7/2012 | Grubert et al. |
| 8,258,070 B2 | 9/2012 | Fujdala et al. |
| 8,278,240 B2 | 10/2012 | Tange et al. |
| 8,294,060 B2 | 10/2012 | Mohanty et al. |
| 8,309,489 B2 | 11/2012 | Cuenya et al. |
| 8,349,761 B2 | 1/2013 | Xia et al. |
| 8,557,727 B2 | 10/2013 | Yin et al. |
| 2001/0004009 A1 | 6/2001 | MacKelvie |
| 2001/0042802 A1 | 11/2001 | Youds |
| 2001/0055554 A1 | 12/2001 | Hoke et al. |
| 2002/0018815 A1 | 2/2002 | Sievers et al. |
| 2002/0068026 A1 | 6/2002 | Murrell et al. |
| 2002/0071800 A1 | 6/2002 | Hoke et al. |
| 2002/0079620 A1 | 6/2002 | DuBuis et al. |
| 2002/0100751 A1 | 8/2002 | Carr |
| 2002/0102674 A1 | 8/2002 | Anderson |
| 2002/0131914 A1 | 9/2002 | Sung |
| 2002/0143417 A1 | 10/2002 | Ito et al. |
| 2002/0182735 A1 | 12/2002 | Kibby et al. |
| 2002/0183191 A1 | 12/2002 | Faber et al. |
| 2002/0192129 A1 | 12/2002 | Shamouilian et al. |
| 2003/0036786 A1 | 2/2003 | Duren et al. |
| 2003/0042232 A1 | 3/2003 | Shimazu |
| 2003/0047617 A1 | 3/2003 | Shanmugham et al. |
| 2003/0066800 A1 | 4/2003 | Saim et al. |
| 2003/0108459 A1 | 6/2003 | Wu et al. |
| 2003/0110931 A1 | 6/2003 | Aghajanian et al. |
| 2003/0129098 A1 | 7/2003 | Endo et al. |
| 2003/0139288 A1 | 7/2003 | Cai et al. |

(56) References Cited

U.S. PATENT DOCUMENTS

| | | |
|---|---|---|
| 2003/0143153 A1 | 7/2003 | Boulos et al. |
| 2003/0172772 A1 | 9/2003 | Sethuram et al. |
| 2003/0223546 A1 | 12/2003 | McGregor et al. |
| 2004/0009118 A1 | 1/2004 | Phillips et al. |
| 2004/0023302 A1 | 2/2004 | Archibald et al. |
| 2004/0023453 A1 | 2/2004 | Xu et al. |
| 2004/0077494 A1 | 4/2004 | LaBarge et al. |
| 2004/0103751 A1 | 6/2004 | Joseph et al. |
| 2004/0109523 A1 | 6/2004 | Singh et al. |
| 2004/0119064 A1 | 6/2004 | Narayan et al. |
| 2004/0127586 A1 | 7/2004 | Jin et al. |
| 2004/0166036 A1 | 8/2004 | Chen et al. |
| 2004/0167009 A1 | 8/2004 | Kuntz et al. |
| 2004/0176246 A1 | 9/2004 | Shirk et al. |
| 2004/0208805 A1 | 10/2004 | Fincke et al. |
| 2004/0213998 A1 | 10/2004 | Hearley et al. |
| 2004/0238345 A1 | 12/2004 | Koulik et al. |
| 2004/0251017 A1 | 12/2004 | Pillion et al. |
| 2004/0251241 A1 | 12/2004 | Blutke et al. |
| 2005/0000321 A1 | 1/2005 | O'Larey et al. |
| 2005/0000950 A1 | 1/2005 | Schroder et al. |
| 2005/0066805 A1 | 3/2005 | Park et al. |
| 2005/0070431 A1 | 3/2005 | Alvin et al. |
| 2005/0077034 A1 | 4/2005 | King |
| 2005/0097988 A1 | 5/2005 | Kodas et al. |
| 2005/0106865 A1 | 5/2005 | Chung et al. |
| 2005/0133121 A1 | 6/2005 | Subramanian et al. |
| 2005/0163673 A1 | 7/2005 | Johnson et al. |
| 2005/0199739 A1 | 9/2005 | Kuroda et al. |
| 2005/0220695 A1 | 10/2005 | Abatzoglou et al. |
| 2005/0227864 A1 | 10/2005 | Sutorik et al. |
| 2005/0233380 A1 | 10/2005 | Pesiri et al. |
| 2005/0240069 A1 | 10/2005 | Polverejan et al. |
| 2005/0258766 A1 | 11/2005 | Kim |
| 2005/0275143 A1 | 12/2005 | Toth |
| 2006/0051505 A1 | 3/2006 | Kortshagen et al. |
| 2006/0068989 A1 | 3/2006 | Ninomiya et al. |
| 2006/0094595 A1 | 5/2006 | Labarge |
| 2006/0096393 A1 | 5/2006 | Pesiri |
| 2006/0105910 A1 | 5/2006 | Zhou et al. |
| 2006/0108332 A1 | 5/2006 | Belashchenko |
| 2006/0153728 A1 | 7/2006 | Schoenung et al. |
| 2006/0153765 A1 | 7/2006 | Pham-Huu et al. |
| 2006/0159596 A1 | 7/2006 | De La Veaux et al. |
| 2006/0166809 A1 | 7/2006 | Malek et al. |
| 2006/0211569 A1 | 9/2006 | Dang et al. |
| 2006/0213326 A1 | 9/2006 | Gollob et al. |
| 2006/0222780 A1 | 10/2006 | Gurevich et al. |
| 2006/0231525 A1 | 10/2006 | Asakawa et al. |
| 2007/0048206 A1 | 3/2007 | Hung et al. |
| 2007/0049484 A1 | 3/2007 | Kear et al. |
| 2007/0063364 A1 | 3/2007 | Hsiao et al. |
| 2007/0084308 A1 | 4/2007 | Nakamura et al. |
| 2007/0084834 A1 | 4/2007 | Hanus et al. |
| 2007/0087934 A1 | 4/2007 | Martens et al. |
| 2007/0163385 A1 | 7/2007 | Takahashi et al. |
| 2007/0173403 A1 | 7/2007 | Koike et al. |
| 2007/0178673 A1 | 8/2007 | Gole et al. |
| 2007/0221404 A1 | 9/2007 | Das et al. |
| 2007/0253874 A1 | 11/2007 | Foret |
| 2007/0292321 A1 | 12/2007 | Plischke et al. |
| 2008/0006954 A1 | 1/2008 | Yubuta et al. |
| 2008/0026041 A1 | 1/2008 | Tepper et al. |
| 2008/0031806 A1 | 2/2008 | Gavenonis et al. |
| 2008/0038578 A1 | 2/2008 | Li |
| 2008/0045405 A1 | 2/2008 | Beutel et al. |
| 2008/0047261 A1 | 2/2008 | Han et al. |
| 2008/0057212 A1 | 3/2008 | Dorier et al. |
| 2008/0064769 A1 | 3/2008 | Sato et al. |
| 2008/0104735 A1 | 5/2008 | Howland |
| 2008/0105083 A1 | 5/2008 | Nakamura et al. |
| 2008/0116178 A1 | 5/2008 | Weidman |
| 2008/0125308 A1 | 5/2008 | Fujdala et al. |
| 2008/0125313 A1 | 5/2008 | Fujdala et al. |
| 2008/0138651 A1 | 6/2008 | Doi et al. |
| 2008/0175936 A1 | 7/2008 | Tokita et al. |
| 2008/0187714 A1 | 8/2008 | Wakamatsu et al. |
| 2008/0206562 A1 | 8/2008 | Stucky et al. |
| 2008/0207858 A1 | 8/2008 | Kowaleski et al. |
| 2008/0248704 A1 | 10/2008 | Mathis et al. |
| 2008/0274344 A1 | 11/2008 | Vieth et al. |
| 2008/0277092 A1 | 11/2008 | Layman et al. |
| 2008/0277264 A1 | 11/2008 | Sprague |
| 2008/0277266 A1 | 11/2008 | Layman |
| 2008/0277267 A1 | 11/2008 | Biberger et al. |
| 2008/0277269 A1 | 11/2008 | Layman et al. |
| 2008/0277270 A1 | 11/2008 | Biberger et al. |
| 2008/0277271 A1 | 11/2008 | Layman |
| 2008/0280049 A1 | 11/2008 | Kevwitch et al. |
| 2008/0280751 A1 | 11/2008 | Harutyunyan et al. |
| 2008/0280756 A1 | 11/2008 | Biberger |
| 2008/0283411 A1 | 11/2008 | Eastman et al. |
| 2008/0283498 A1 | 11/2008 | Yamazaki |
| 2009/0010801 A1 | 1/2009 | Murphy et al. |
| 2009/0054230 A1 | 2/2009 | Veeraraghavan et al. |
| 2009/0088585 A1 | 4/2009 | Schammel et al. |
| 2009/0092887 A1 | 4/2009 | McGrath et al. |
| 2009/0098402 A1 | 4/2009 | Kang et al. |
| 2009/0114568 A1 | 5/2009 | Trevino et al. |
| 2009/0162991 A1 | 6/2009 | Beneyton et al. |
| 2009/0168506 A1 | 7/2009 | Han et al. |
| 2009/0170242 A1 | 7/2009 | Lin et al. |
| 2009/0181474 A1 | 7/2009 | Nagai |
| 2009/0200180 A1 | 8/2009 | Capote et al. |
| 2009/0208367 A1 | 8/2009 | Calio et al. |
| 2009/0209408 A1 | 8/2009 | Kitamura et al. |
| 2009/0223410 A1 | 9/2009 | Jun et al. |
| 2009/0253037 A1 | 10/2009 | Park et al. |
| 2009/0274897 A1 | 11/2009 | Kaner et al. |
| 2009/0274903 A1 | 11/2009 | Addiego |
| 2009/0286899 A1 | 11/2009 | Hofmann et al. |
| 2009/0324468 A1 | 12/2009 | Golden et al. |
| 2010/0089002 A1 | 4/2010 | Merkel |
| 2010/0092358 A1 | 4/2010 | Koegel et al. |
| 2010/0124514 A1 | 5/2010 | Chelluri et al. |
| 2010/0166629 A1 | 7/2010 | Deeba |
| 2010/0180581 A1 | 7/2010 | Grubert et al. |
| 2010/0180582 A1 | 7/2010 | Mueller-Stach et al. |
| 2010/0186375 A1 | 7/2010 | Kazi et al. |
| 2010/0240525 A1 | 9/2010 | Golden et al. |
| 2010/0275781 A1 | 11/2010 | Tsangaris |
| 2011/0006463 A1 | 1/2011 | Layman |
| 2011/0052467 A1 | 3/2011 | Chase et al. |
| 2011/0143041 A1 | 6/2011 | Layman et al. |
| 2011/0143915 A1 | 6/2011 | Yin et al. |
| 2011/0143916 A1 | 6/2011 | Leamon |
| 2011/0143926 A1 | 6/2011 | Yin et al. |
| 2011/0143930 A1 | 6/2011 | Yin et al. |
| 2011/0143933 A1 | 6/2011 | Yin et al. |
| 2011/0144382 A1 | 6/2011 | Yin et al. |
| 2011/0152550 A1 | 6/2011 | Grey et al. |
| 2011/0158871 A1 | 6/2011 | Arnold et al. |
| 2011/0174604 A1 | 7/2011 | Duesel et al. |
| 2011/0243808 A1 | 10/2011 | Fossey et al. |
| 2011/0245073 A1 | 10/2011 | Oljaca et al. |
| 2011/0247336 A9 | 10/2011 | Farsad et al. |
| 2011/0305612 A1 | 12/2011 | Müller-Stach et al. |
| 2012/0023909 A1 | 2/2012 | Lambert et al. |
| 2012/0045373 A1 | 2/2012 | Biberger |
| 2012/0097033 A1 | 4/2012 | Arnold et al. |
| 2012/0122660 A1 | 5/2012 | Andersen et al. |
| 2012/0124974 A1 | 5/2012 | Li et al. |
| 2012/0171098 A1 | 7/2012 | Hung et al. |
| 2012/0308467 A1 | 12/2012 | Carpenter et al. |
| 2013/0213018 A1 | 8/2013 | Yin et al. |
| 2013/0280528 A1 | 10/2013 | Biberger |
| 2013/0281288 A1 | 10/2013 | Biberger et al. |
| 2013/0316896 A1 | 11/2013 | Biberger |

(56) References Cited

U.S. PATENT DOCUMENTS

| | | | |
|---|---|---|---|
| 2013/0345047 | A1 | 12/2013 | Biberger et al. |
| 2014/0018230 | A1 | 1/2014 | Yin et al. |

FOREIGN PATENT DOCUMENTS

| | | | |
|---|---|---|---|
| EP | 1 256 378 | A2 | 11/2002 |
| EP | 1 619 168 | A1 | 1/2006 |
| GB | 1 307 941 | A | 2/1973 |
| JP | 56-146804 | A | 11/1981 |
| JP | 61-086815 | A | 5/1986 |
| JP | 62-102827 | A | 5/1987 |
| JP | 63-214342 | A | 9/1988 |
| JP | 1-164795 | A | 6/1989 |
| JP | 05-228361 | A | 9/1993 |
| JP | 05-324094 | A | 12/1993 |
| JP | 6-93309 | A | 4/1994 |
| JP | 6-135797 | A | 5/1994 |
| JP | 6-065772 | U | 9/1994 |
| JP | 6-272012 | A | 9/1994 |
| JP | 07-031873 | A | 2/1995 |
| JP | 07-256116 | A | 10/1995 |
| JP | 8-158033 | A | 6/1996 |
| JP | 10-130810 | A | 5/1998 |
| JP | 11-502760 | A | 3/1999 |
| JP | 2000-220978 | A | 8/2000 |
| JP | 2002-88486 | A | 3/2002 |
| JP | 2002-336688 | A | 11/2002 |
| JP | 2003-126694 | A | 5/2003 |
| JP | 2004-233007 | A | 8/2004 |
| JP | 2004-249206 | A | 9/2004 |
| JP | 2004-290730 | A | 10/2004 |
| JP | 2005-503250 | A | 2/2005 |
| JP | 2005-122621 | A | 5/2005 |
| JP | 2005-218937 | A | 8/2005 |
| JP | 2005-342615 | A | 12/2005 |
| JP | 2006-001779 | A | 1/2006 |
| JP | 2006-508885 | A | 3/2006 |
| JP | 2006-247446 | A | 9/2006 |
| JP | 2006-260385 | A | 9/2006 |
| JP | 2007-46162 | A | 2/2007 |
| JP | 2007-203129 | A | 8/2007 |
| SU | 493241 | A | 3/1976 |
| TW | 200611449 | | 4/2006 |
| TW | 201023207 | A | 6/2010 |
| WO | WO-96/28577 | A1 | 9/1996 |
| WO | WO-02/092503 | A1 | 11/2002 |
| WO | WO-2004/052778 | A2 | 6/2004 |
| WO | WO-2005/063390 | A1 | 7/2005 |
| WO | WO 2006/079213 | A1 | 8/2006 |
| WO | WO-2008/130451 | A2 | 10/2008 |
| WO | WO-2008/130451 | A3 | 10/2008 |
| WO | WO-2011/081833 | A1 | 7/2011 |

OTHER PUBLICATIONS

Carrot, G. et al. (Sep. 17, 2002). "Surface-Initiated Ring-Opening Polymerization: A Versatile Method for Nanoparticle Ordering," *Macromolecules* 35(22):8400-8404.

Chen, H.-S. et al. (Jul. 3, 2001). "On the Photoluminescence of Si Nanoparticles," *Mater. Phys. Mech.* 4:62-66.

Faber, K. T. et al. (Sep. 1988). "Toughening by Stress-Induced Microcracking in Two-Phase Ceramics," Communications of the American Ceramic Society 71(9): C-399-C401.

Fauchais, P. et al. (Jun. 1989). "La Projection Par Plasma: Une Revue," *Ann. Phys. Fr.* 14(3):261-310.

Fauchais, P. et al. (Jan. 1993). "Les Dépôts Par Plasma Thermique,"*Revue Générale De L'Electricité*, RGE, Paris, France, No. 2, pp. 7-12 (in French).

Fauchais, P. et al. (Jan. 1996). "Plasma Spray: Study of the Coating Generation," *Ceramics International* 22(4):295-303.

Fojtik, A. et al. (Apr. 29, 1994). "Luminescent Colloidal Silicon Particles," *Chemical Physics Letters* 221 :363-367.

Fojtik, A. (Jan. 13, 2006). "Surface Chemistry of Luminescent Colloidal Silicon Nanoparticles," *J. Phys. Chem. B*. 110(5):1994-1998.

Gutsch, A. et al. (2002). "Gas-Phase Production of Nanoparticles," *Kona* No. 20, pp. 24-37.

Han, B. Q. et al. (Jan. 2004). "Deformation Mechanisms and Ductility of Nanostructured Al Alloys", *Mat. Res. Soc. Symp. Proc.* 821:P9.1.1-P9.1.6.

Heberlein, J. (2002). "New Approaches in Thermal Plasma Technology", *Pure Appl. Chem.* 74(3):327-335.

Hua, F. et al. (Mar. 2006). "Organically Capped Silicon Nanoparticles With Blue Photoluminescence Prepared by Hydrosilylation Followed by Oxidation," *Langmuir* 22(9):4363-4370.

Ji, Y. et al. (Nov. 2002) "Processing and Mechanical Properties of $Al_2O_3$-5 vol.% Cr Nanocomposites," *Journal of the European Ceramic Society* 22(12):1927-1936.

Jouet, R. J. et al. (Jan. 25, 2005). "Surface Passivation of Bare Aluminum Nanoparticles Using Perfluoroalkyl Carboxylic Acids," *Chem. Mater.*17(11):2987-2996.

Kenvin, J. C. et al. (1992). "Supported Catalysts Prepared from Mononuclear Copper Complexes: Catalytic Properties", *J. Catalysis* 135:81-91.

Konrad, H. et al. (1996). "Nanostructured Cu-Bi Alloys Prepared by Co-Evaporation in a Continuous Gas Flow," *NanoStructured Materials* 7(6):605-610.

Kim, N. Y. et al. (Mar. 5, 1997). "Thermal Derivatization of Porous Silicon with Alcohols," *J. Am. Chem. Soc.* 119(9):2297-2298.

Kwon, Y.-S. et al. (Apr. 30, 2003). "Passivation Process for Superfine Aluminum Powders Obtained by Electrical Explosion of Wires," *Applied Surface Science* 211:57-67.

Langner, A. et al. (Aug. 25, 2005). "Controlled Silicon Surface Functionalization by Alkene Hydrosilylation," *J. Am. Chem. Soc.* 127(37):12798-12799.

Li, D. et al. (Apr. 9, 2005). "Environmentally Responsive "Hairy" Nanoparticles: Mixed Homopolymer Brushes on Silica Nanoparticles Synthesized by Living Radical Polymerization Techniques," *J. Am. Chem. Soc.* 127(7):6248-6256.

Li, X. et al. (May 25, 2004). "Surface Functionalization of Silicon Nanoparticles Produced by Laser-Driven Pyrolysis of Silane Followed by HF-$HNO_3$ Etching," *Langmuir* 20(11):4720-4727.

Liao, Y.-C. et al. (Jun. 27, 2006). "Self-Assembly of Organic Monolayers on Aerosolized Silicon Nanoparticles," *J.Am. Chem. Soc.* 128(28):9061-9065.

Liu, S.-M. et al. (Jan. 13, 2006). "Enhanced Photoluminescence from Si Nano-Organosols by Functionalization With Alkenes and Their Size Evolution," *Chem. Mater.* 18(3):637-642.

Mühlenweg, H. et al. (2004). "Gas-Phase Reactions—Open Up New Roads to Nanoproducts," *Degussa ScienceNewsletter* No. 08, pp. 12-16.

Nagai, Y. et al. (Jul. 3, 2006). "Sintering Inhibition Mechanism of Platinum Supported on Ceria-Based Oxide and Pt-Oxide-Support Interaction," *J. Catalysis* 242:103-109.

NASA (2009). "Enthalpy," Article located at http://www.grc.nasa.gov/WWW/K-12/airplane/enthalpy.htrnl, published by National Aeronautics and Space Administration on Nov. 23, 2009, 1 page.

Neiner, D. (Aug. 5, 2006). "Low-Temperature Solution Route to Macroscopic Amounts of Hydrogen Terminated Silicon Nanoparticles," *J. Am. Chem. Soc.* 128:11016-11017.

Netzer, L. et al. (1983). "A New Approach to Construction of Artificial Monolayer Assemblies," *J. Am. Chem. Soc.* 105(3):674-676.

"Platinum Group Metals: Annual Review 1996" (Oct. 1997). Engineering and Mining Journal, p. 63.

Rahaman, R. A. et al. (1995). "Synthesis of Powders," in *Ceramic Processing and Sintering*. Marcel Decker, Inc., NewYork, pp. 71-77.

Sailor, M. J. (1997). "Surface Chemistry of Luminescent Silicon Nanocrystallites," *Adv. Mater.* 9(10):783-793.

Stiles, A. B. (Jan. 1, 1987). "Manufacture of Carbon-Supported Metal Catalysts," in *Catalyst Supports and Supported Catalysts*, Butterworth Publishers, MA, pp. 125-132.

Subramanian, S. et al. (1991). "Structure and Activity of Composite Oxide Supported Platinum-Iridium Catalysts," *Applied Catalysts* 74: 65-81.

Tao, Y.-T. (May 1993). "Structural Comparison of Self-Assembled Monolayers of *n*-Alkanoic Acids on the surfaces of Silver, Copper, and Aluminum," *J. Am. Chem. Soc.* 115(10):4350-4358.

(56) References Cited

OTHER PUBLICATIONS

Ünal, N. et al. (Nov. 2011). "Influence of WC Particles on the Microstructural and Mechanical Properties of 3 mol% $Y_2O_3$ Stabilized $ZrO_2$ Matrix Composites Produced by Hot Pressing," Journal of the European Ceramic Society (31)13: 2267-2275.
Vardelle, A. et al. (1996). "Coating Generation: Vaporization of Particles in Plasma Spraying and Splat Formation," Universite de Limoges, 123 Avenue A. Thomas 87000, Limoges, France, *Pure & Appl. Chem.* 68(5):1093-1099.
Vardelle, M. et al. (Jun. 1991). "Experimental Investigation of Powder Vaporization in Thermal Plasma Jets," *Plasma Chemistry and Plasma Processing* 11(2):185-201.
Yoshida, T. (1994). "The Future of Thermal Plasma Processing for Coating", *Pure & Appl. Chem.* 66(6):1223-1230.
Zou, J. et al. (Jun. 4, 2004). "Solution Synthesis of Ultrastable Luminescent Siloxane-Coated Silicon Nanoparticles," *Nano Letters* 4(7):1181-1186.
Non Final Office Action mailed on Feb. 19, 2010, for U.S. Appl. No. 12/152,109, filed May 9, 2008, Biberger et al., 17 pages.
Non Final Office Action mailed on Feb. 18, 2010, for U.S. Appl. No. 12/001,644, filed Dec. 11, 2007, for Biberger et al., 8 pages.
International Search Report mailed on Aug. 8, 2008, for PCT Patent Application No. PCT/US2008/06093, filed May 12, 2008, published on Nov. 20, 2008, as WO 2008/140823, 1 page.
Written Opinion mailed on Aug. 8, 2008, for PCT Patent Application No. PCT/US2008/06093, filed May 12, 2008, published on Nov. 20, 2008, as WO 2008/140823, 8 pages.
U.S. Appl. No. 13/291,983, filed Nov. 8, 2011, for Layman et al.
U.S. Appl. No. 12/152,084, filed May 9, 2008, for Biberger.
U.S. Appl. No. 13/028,693, filed Feb. 16, 2011, for Biberger.
U.S. Appl. No. 12/943,909, filed Nov. 10, 2010, for Layman.
U.S. Appl. No. 12/152,111, filed May 9, 2008, for Biberger et al.
U.S. Appl. No. 12/151,830, filed May 8, 2008, for Biberger et al.
U.S. Appl. No. 12/968,248, filed Dec. 14, 2010, for Biberger.
U.S. Appl. No. 12/968,245, filed Dec. 14, 2010, for Biberger.
U.S. Appl. No. 12/968,241, filed Dec. 14, 2010, for Biberger.
U.S. Appl. No. 12/968,239, filed Dec. 14, 2010, for Biberger.
U.S. Appl. No. 12/969,128, filed Dec. 15, 2010, for Biberger.
U.S. Appl. No. 12/962,463, filed Dec. 7, 2010, for Leamon.
U.S. Appl. No. 12/961,030, filed Dec. 6, 2010, for Lehman.
U.S. Appl. No. 12/961,108, filed Dec. 6, 2010, for Lehman.
U.S. Appl. No. 12/961,200, filed Dec. 6, 2010, for Lehman.
U.S. Appl. No. 12/968,253, filed Dec. 14, 2010, for Biberger.
U.S. Appl. No. 12/968,235, filed Dec. 14, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,087, filed Dec. 15, 2010, for Biberger.
U.S. Appl. No. 12/962,533, filed Dec. 7, 2010, for Yin et al.
U.S. Appl. No. 12/962,523, filed Dec. 7, 2010, for Yin et al.
U.S. Appl. No. 12/001,643, filed Dec. 11, 2007, for Biberger et al.
U.S. Appl. No. 12/474,081, filed May 28, 2009, for Biberger et al.
U.S. Appl. No. 12/001,602, filed Dec. 11, 2007, for Biberger et al.
U.S. Appl. No. 12/001,644, filed Dec. 11, 2007, for Biberger et al.
U.S. Appl. No. 12/969,457, filed Nov. 15, 2010, for Leamon et al.
U.S. Appl. No. 12/969,503, filed Nov. 15, 2010, for Leamon et al.
U.S. Appl. No. 12/954,813, filed Nov. 26, 2010, for Biberger.
U.S. Appl. No. 12/954,822, filed Nov. 26, 2010, for Biberger.
U.S. Appl. No. 13/033,514, filed Feb. 23, 2011, for Biberger et al.
U.S. Appl. No. 13/589,024, filed Aug. 17, 2012, for Yin et al.
U.S. Appl. No. 13/801,726, filed Mar. 13, 2013, for Qi et al.
Babin, A. et al. (1985). "Solvents Used in the Arts," *Center for Safety in the Arts*: 16 pages.
Chen, W.-J. et al. (Mar. 18, 2008). "Functional $Fe_3O_4/TiO_2$ Core/Shell Magnetic Nanoparticles as Photokilling Agents for Pathogenic Bacteria," *Small* 4(4): 485-491.
Gangeri, M. et al. (2009). "Fe and Pt Carbon Nanotubes for the Electrocatalytic Conversion of Carbon Dioxide to Oxygenates," *Catalysis Today* 143: 57-63.
Luo, J. et al. (2008). "Core/Shell Nanoparticles as Electrocatalysts for Fuel Cell Reactions," *Advanced Materials* 20: 4342-4347.
Mignard, D. et al. (2003). "Methanol Synthesis from Flue-Gas $CO_2$ and Renewable Electricity: A Feasibility Study," *International Journal of Hydrogen Energy* 28: 455-464.
Park, H.-Y. et al. (May 30, 2007). "Fabrication of Magnetic Core@Shell Fe Oxide@Au Nanoparticles for Interfacial Bioactivity and Bio-Separation," *Langmuir* 23: 9050-9056.
Park, N.-G. et al. (Feb. 17, 2004). "Morphological and Photoelectrochemical Characterization of Core-Shell Nanoparticle Films for Dye-Sensitized Solar Cells: Zn-O Type Shell on $SnO_2$ and $TiO_2$ Cores," *Langmuir* 20: 4246-4253.
"Plasma Spray and Wire Flame Spray Product Group," located at http://www.processmaterials.com/spray.html, published by Process Materials, Inc., last accessed Aug. 5, 2013, 2 pages.
Chaim, R. et al. (2009). "Densification of Nanocrystalline $Y_2O_3$ Ceramic Powder by Spark Plasma Sintering," *Journal of European Ceramic Society* 29: 91-98.
Viswanathan, V. et al. (2006). "Challenges and Advances in Nanocomposite Processing Techniques," *Materials Science and Engineering* R 54: 121-285.

FLUID RECIRCULATION SYSTEM FOR USE IN VAPOR PHASE PARTICLE PRODUCTION SYSTEM

The present application is a divisional of U.S. patent application Ser. No. 12/151,765, filed May 8, 2008 which claims priority benefit of U.S. Provisional Patent Application Ser. No. 60/928,946, filed May 11, 2007, entitled "MATERIAL PRODUCTION SYSTEM AND METHOD," both of which are hereby incorporated by reference in their entireties as if set forth herein. The entire contents of U.S. patent application Ser. No. 11/110,341, filed on Apr. 19, 2005, entitled, "HIGH THROUGHPUT DISCOVERY OF MATERIALS THROUGH VAPOR PHASE SYNTHESIS" are incorporated by reference herein.

FIELD OF THE INVENTION

The present invention relates generally to the field of particle production. More specifically, the present invention relates to systems and methods for recirculating fluid used within a vapor phase particle production system.

BACKGROUND OF THE INVENTION

Many vapor phase particle production systems produce mixtures of particles and fluid. Typically, these mixtures are high in temperature and thus reactive. In some systems, these mixtures are quenched via introduction of a conditioning fluid. The conditioning fluid acts to cool the mixture and promote particle formation, and often acts as a carrier for the particles. Typically, particles are sampled or collected from the mixture following introduction of the conditioning fluid. Then, the conditioning fluid is vented to the ambient, or otherwise disposed. This disposal occurs because typical particle production systems require high purity gases as conditioning fluids. In many cases, the purity must be on the order of 99.9999% purity. The unit cost of particles produced using these methods is inflated by the need to use fresh fluid for each production run.

What is needed in the art is a way to reduce the costs associated with a vapor phase particle production system, while at the same time maintaining a high purity level for the system.

SUMMARY OF THE INVENTION

In one aspect of the present invention, a particle production system comprises a particle production core and a fluid recirculation system fluidly coupled to the particle production core. The production core is configured to produce a reactive particle-gas mixture from a precursor material and a working gas, and to quench the reactive particle-gas mixture using a conditioning fluid, thereby producing a cooled particle-gas mixture. The cooled particle-gas mixture comprises a plurality of precursor material particles and an output fluid. The output fluid includes the conditioning fluid. The fluid recirculation system is configured to receive the cooled particle-gas mixture from the particle production core, and to remove the plurality of precursor material particles from the cooled particle-gas mixture, thereby producing a filtered output that includes the output fluid. The fluid recirculation system is also configured to modulate a content ratio of the filtered output, thereby producing a content-controlled, filtered output, wherein the filtered output comprises a distinct primary fluid and a distinct secondary fluid, and the content ratio is the ratio of the primary fluid to the secondary fluid. The fluid recirculation system is further configured to channel the content-controlled, filtered output to the particle production core, wherein the content-controlled, filtered output is provided to the particle production core as the conditioning fluid to be used in quenching the reactive particle-gas mixture.

In a preferred embodiment, the particle production core comprises a particle production reactor and a quench chamber fluidly coupled to the particle production reactor. The particle production reactor is configured to receive the precursor material and the working gas, to energize the working gas to form a plasma, and to apply the plasma to the precursor material, thereby producing the reactive particle-gas mixture. The quench chamber is configured to receive the reactive particle-gas mixture from the particle production reactor, to receive the content-controlled, filtered output from the recirculation system as the conditioning fluid, and to mix the received conditioning fluid with the reactive particle-gas mixture, thereby producing the cooled particle-gas mixture.

In some embodiments, the fluid recirculation system is further configured to control the temperature of the filtered output prior to modulation of the content ratio.

Furthermore, in some embodiments, the fluid recirculation system is further configured to sense the ratio between the primary fluid and the secondary fluid, and to modulate the content ratio of the filtered output by adjusting the amount of either the primary fluid or the secondary fluid in the content-controlled, filtered output based on the sensed ratio.

In another aspect of the present invention, a particle production system comprises a particle production reactor and a quench chamber having a fluid inlet, a reactive mixture inlet fluidly coupled to the particle production reactor, and a cooled mixture outlet. The particle production system also comprises a filter element fluidly coupled to the cooled mixture outlet, a temperature control module fluidly coupled to the filter element, a content ratio control module fluidly coupled to the temperature control module, and a channeling element fluidly coupling the content ratio control module to the fluid inlet of the quench chamber.

The particle production reactor is configured to produce a reactive particle-gas mixture from a precursor material and a working gas. The quench chamber is configured to receive a conditioning fluid at the fluid inlet, to receive the reactive particle-gas mixture mix fluid from the particle production reactor at the reactive mixture inlet, and to mix the conditioning fluid with the reactive particle-gas mixture to produce a cooled particle-gas mixture. The cooled particle-gas mixture comprises a plurality of precursor material particles and an output fluid, the output fluid including the conditioning fluid. The filter element is configured to receive and filter the output fluid from the quench chamber to produce a filtered output. The temperature control module is configured to control the temperature of the filtered output to produce a temperature-controlled, filtered output. The content ratio control module is configured to modulate a content ratio of the temperature-controlled, filtered output, thereby producing a content-controlled, temperature-controlled, filtered output, wherein the temperature-controlled, filtered output comprises a distinct primary fluid and a distinct secondary fluid, and the content ratio is the ratio of the primary fluid to the secondary fluid. Finally, the channeling element is configured to supply the content-controlled, temperature-controlled, filtered output to the fluid inlet of the quench chamber, wherein the content-controlled, filtered output is provided to the quench chamber as the conditioning fluid to be used in quenching the reactive particle-gas mixture.

In a preferred embodiment, the particle production reactor is configured to energize the working gas to form a plasma, and to apply the plasma to the precursor material, thereby producing the reactive particle-gas mixture.

In some embodiments, the system also comprises a suction generator configured to generate a suction force at the cooled mixture outlet of the quench chamber to draw the output fluid from the quench chamber.

In some embodiments, the filter element is configured to remove the plurality of precursor material particles from the output fluid to produce the filtered output. Furthermore, the filter element preferably comprises a high efficiency particulate air (HEPA) filter.

In some embodiments, a pressure relief module is fluidly coupled between the filter element and the temperature control module. This pressure relief module is configured to reduce the pressure of the filtered output if the pressure exceeds a predetermined threshold.

In some embodiments, the temperature control module comprises a heat exchanger. It is also contemplated that other means for adjusting fluid temperature can be employed.

In a preferred embodiment, the content ratio control module comprises a sensor and a micro-controller communicatively connected to the sensor. The sensor is configured to sense the content ratio of the temperature-controlled, filtered output, and to produce a signal representing the sensed content ratio. The micro-controller is configured to receive the signal from the sensor and modulate the content ratio of the content-controlled, temperature-controlled, filtered output that is to be supplied to the fluid inlet of the quench chamber. This modulation is based on the received signal.

In some embodiments, the content ratio control module can further comprise a buffer reservoir fluidly coupled to the temperature control module and to the sensor. The buffer reservoir is configured to receive the temperature-controlled, filtered output from the temperature control module and to temporarily store the temperature-controlled, filtered output before the content ratio of the temperature-controlled, filtered output is modulated. The content ratio control module can also comprise a fluid relief valve fluidly coupled between the buffer reservoir and the ambient atmosphere. This fluid relief valve is configured to vent the secondary fluid from the buffer reservoir to the ambient atmosphere.

Furthermore, the content ratio control module can comprise a secondary fluid supply reservoir that stores a supply of the secondary fluid and is communicatively connected to the micro-controller. This secondary fluid supply reservoir is configured to selectively add a portion of the secondary fluid from the secondary fluid supply reservoir into the temperature-controlled, filtered output in response to a signal from the micro-controller, thereby producing the content-controlled, temperature-controlled, filtered output.

The content ratio control module can additionally or alternatively comprise a primary fluid supply reservoir that stores a supply of the primary fluid and is communicatively connected to the micro-controller. The primary fluid supply reservoir is configured to selectively add a portion of the primary fluid from the primary fluid supply reservoir into the temperature-controlled, filtered output in response to a signal from the micro-controller, thereby producing the content-controlled, temperature-controlled, filtered output.

In addition to these systems, the present invention also includes methods of recirculating fluid within these systems, involving the operations discussed both above and below.

DETAILED DESCRIPTION OF THE INVENTION

Figure 1:
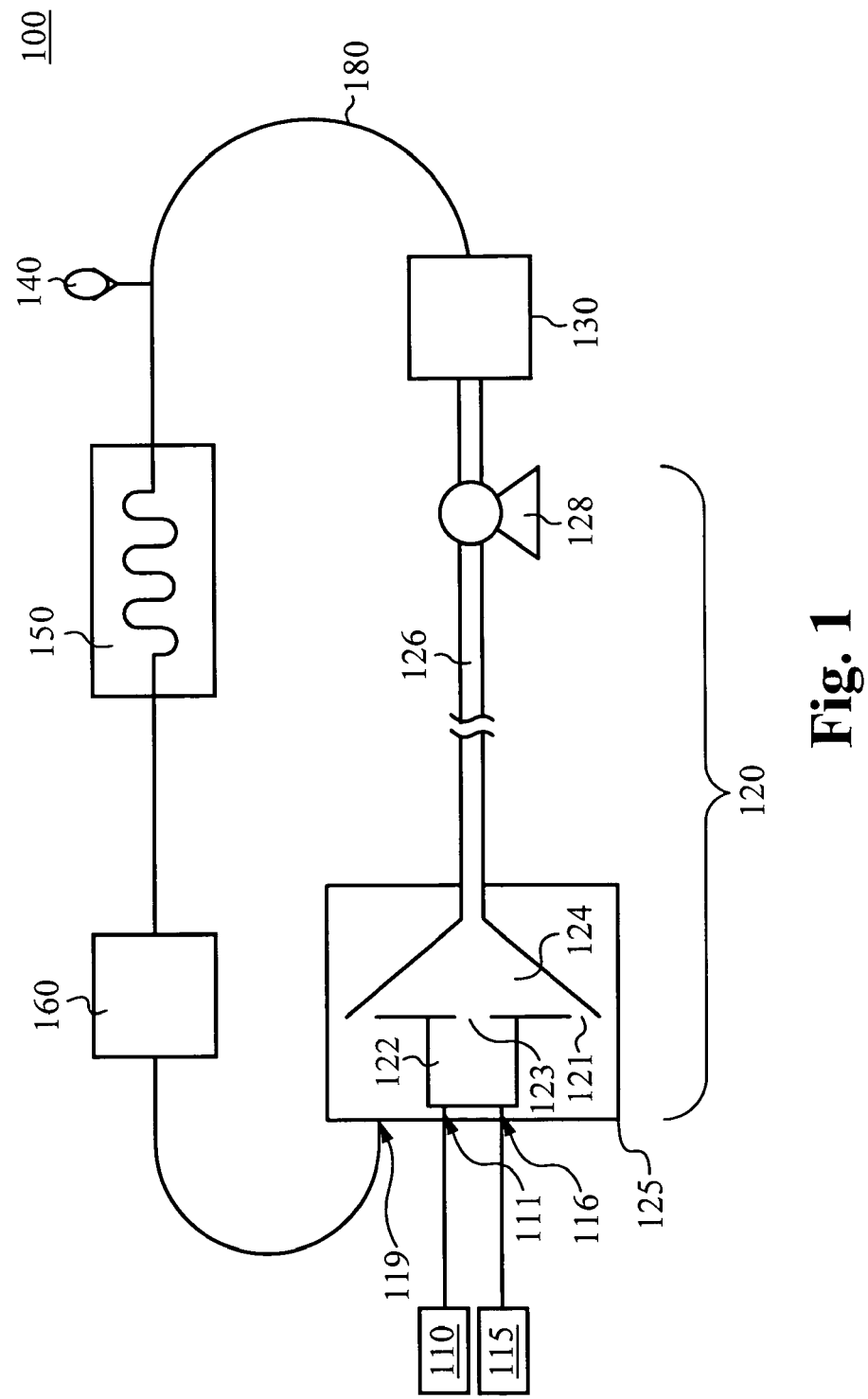
FIG. 1 is a schematic illustration of one embodiment of a fluid recirculation system integrated into a particle production system in accordance with the principles of the present invention.

The description below concerns several embodiments of the invention. The discussion references the illustrated preferred embodiment. However, the scope of the present invention is not limited to either the illustrated embodiment, nor is it limited to those discussed. To the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles.

The present invention will be readily understood by the following detailed description in conjunction with the accompanying drawings. To facilitate this description, like reference numerals designate like elements.

FIG. 1 illustrates one embodiment of a fluid recirculation system integrated into a particle production system 100 in accordance with the principles of the present invention. The particle production system 100 includes a particle production core 120, which takes various material inputs, including both working and conditioning fluids as well as particle precursors, and produces a particle-gas mixture. The two main components of the particle production core 120 are a particle production reactor 122, configured to produce a reactive particle-gas mixture from a precursor material and a working gas, and a quench chamber 124, configured to quench the reactive particle-gas mixture using a conditioning fluid.

In general, vapor phase particle production means are preferred for producing the particle-gas mixture in the particle production core 120. Most preferably, the embodiments of the present invention use particle production systems similar to those disclosed in U.S. Pat. application Ser. No. 11/110,341, filed on Apr. 19, 2005 and entitled, "HIGH THROUGHPUT DISCOVERY OF MATERIALS THROUGH VAPOR PHASE SYNTHESIS", which is currently published as U.S. Publication No. 2005-0233380-A. In such a particle production system, working gas is supplied from a gas source to a plasma reactor. Within the plasma reactor, energy is delivered to the working gas, thereby creating a plasma. A variety of different means can be employed to deliver this energy, including, but not limited to, DC coupling, capacitive coupling, inductive coupling, and resonant coupling. One or more material dispensing devices introduce at least one material, preferably in powder form, into the plasma reactor. The combination within the plasma reactor of the plasma and the material(s) introduced by the material dispensing device(s) forms a highly reactive and energetic mixture, wherein the powder can be vaporized. This mixture of vaporized powder moves through the plasma reactor in the flow direction of the working gas. As it moves, the mixture cools and particles are formed therein. The still-energetic output mixture, comprising hot gas and energetic particles, is emitted from the plasma reactor. Following emission from the plasma reactor, the output mixture can cool further. This output mixture may comprise hot gas and particles of relatively homogeneous size distribution. Each particle can comprise a combination of the materials introduced by the material dispensing devices. It is contemplated that portions of these or other particle production means, including non-vapor phase particle production means, are within the scope of the present invention as well and can be employed as part of the particle production core 120.

In a preferred embodiment, the reactor 122 is fluidly coupled to a working gas supply 110 via a working gas inlet 111, thereby allowing the reactor 122 to receive a working gas from the working gas supply 110. Examples of working gas include, but are not limited to, argon and hydrogen. The reactor 122 can also be fluidly coupled to a precursor material supply 115 via a precursor material inlet 116, thereby allowing the reactor 122 to receive precursor material, such as precursor material powder, from the precursor material supply 115. The reactor 122 combines the working gas and the precursor material to produce a reactive particle-gas mixture. In a preferred embodiment, as discussed above, energy is delivered to the working gas within the reactor 122, thereby creating a plasma. The plasma is then applied to the precursor material. The application of the plasma to the precursor material(s) forms a highly reactive and energetic mixture, wherein the powder can be vaporized. This mixture of vaporized powder moves through the reactor 122 in the flow direction of the working gas. This reactive particle-gas mixture flows into the quench chamber 124, preferably via reactive mixture port 123, which fluidly couples the reactor 122 to the quench chamber 124.

In addition to being configured to receive the reactive mixture from the reactor 122, the quench chamber 124 is also configured to receive recirculated conditioning fluid. One example of a conditioning fluid is argon. However, it is contemplated that other fluids may be used in addition to or as alternatives to argon. In a preferred embodiment, the quench chamber 124 is housed within a conditioning fluid input manifold 125, which itself receives recirculated conditioning fluid through a conditioning fluid inlet 119. The conditioning fluid is supplied to the conditioning fluid input manifold 125 via a recirculation system discussed in detail below. The manifold 125 is fluidly coupled to the quench chamber 124, preferably via one or more conditioning fluid ports 121, thereby providing the recirculated conditioning fluid to the quench chamber 124.

The quench chamber 124 mixes the conditioning fluid with the reactive particle-gas mixture from the reactor 122, thereby quenching the reactive particle-gas mixture. This quenching rapidly cools the reactive mixture to form a cooled particle-gas mixture. The cooled mixture is preferably drawn into a conduit system 126 that is fluidly coupled to the quench chamber. In a preferred embodiment, the cooled mixture is drawn into the conduit system 126 by suction supplied by a suction generator 128, such as a pump, drawing the cooled mixture towards the suction generator 128. A powder product can be sampled or collected from the cooled mixture between the quench chamber 124 and the suction generator 128. Such sampling or collection can be achieved in a variety of ways.

Outside of the quench chamber 124 and the particle production core 120, the rest of the particle production system 100 comprises a fluid recirculation system, which includes a plurality of elements fluidly coupled via a conduit system 180. The fluid recirculation system is configured to receive the cooled mixture from the particle production core, filter the cooled mixture to produce a filtered output, modulate the content ratio of the filtered output to produce a content-controlled, filtered output, and channel the content-controlled, filtered output to the particle production core 120 to be used as the recirculated conditioning fluid in quenching the reactive mixture. The means for performing these operations, as well as other functions, will be discussed in further detail below.

In a preferred embodiment, the fluid recirculation system comprises a filter element 130 fluidly coupled to the suction generator, a pressure relief module 140 fluidly coupled to the filter element 130, a temperature control module 150 fluidly coupled to the pressure relief module 140, and a content ratio control module 160 fluidly coupled to the temperature control module 150 and to the particle production core 120, thereby creating a recirculation path from the output of the particle production core 120 to the input of the particle production core 120. It is contemplated that the scope of the present invention can include the rearrangement or removal of some of these components. For example, pressure relief module 140 may be disposed between temperature control module 150 and content control module 160, rather than between filter element 130 and temperature control module 150. In an alternative example, pressure relief module 140 can be completely removed from the fluid recirculation path.

The suction generator 128 preferably moves the cooled particle-gas mixture out of the particle production core through the conduit system 126 and into the filter element 130. The filter element 130 is configured to remove remaining particles, such as precursor material particles, from the cooled mixture, thereby producing a filtered output. Preferably, the filter element 130 is a high efficiency particulate air (HEPA) filter. In some embodiments, the filter element 130 does not completely remove all of the particles from the cooled mixture.

Following passage through the filter element 130, the cooled mixture becomes a filtered output, which is channeled into the conduit system 180. The conduit system 180 fluidly couples the filter element 130 to the pressure relief module 140 such that the pressure relief module 140 can receive the filtered output from the filter element 130. The pressure relief module 140 is configured to reduce the pressure of the fluid of the filtered output. This pressure reduction can be conditioned upon the pressure of the fluid exceeding a predetermined threshold. Furthermore, this pressure reduction can be achieved in a variety of ways, including, but not limited to, venting to ambient atmosphere. As noted above, in some embodiments, no pressure relief module 140 is included at all.

Following passage through the pressure relief module 140, the filtered output passes into the temperature control module 150. The temperature control module 150 is configured to regulate the temperature of the output, thereby forming a temperature-controlled, filtered output. In a preferred embodiment, the temperature control module 150 comprises a heat exchanger. Additionally, in some embodiments, no temperature control module 150 is included at all.

The temperature-controlled, filtered output reenters a portion of the conduit system 180 that fluidly couples the temperature control module 150 to the content ratio control module 160. The content ratio control module 160 is configured to receive and modulate the content ratio of the temperature-controlled, filtered output, thereby producing a content-controlled, temperature-controlled, filtered output. In a preferred embodiment, the filtered output that is received by the content control module 160 comprises a distinct primary fluid and a distinct secondary fluid. The content control module 160 controls the ratio of the primary fluid to the secondary fluid, making adjustments when necessary, thereby producing the content-controlled output.

This content-controlled output, still comprising conditioning fluid from the quench chamber, is then channeled through another portion of the conduit system 180 to the conditioning fluid inlet 119 of the particle production core 120 for use in quenching. Thus, the output of the quench chamber 124, which includes the conditioning fluid, has been recirculated back into the quench chamber 124. This recirculation includes the filtering and the content control (and in some cases, the pressure relief and the temperature control) of the fluid to ensure sufficient preparation for the fluid's reuse in quenching the reactive mixture in the particle production core 120.

Figure 2:
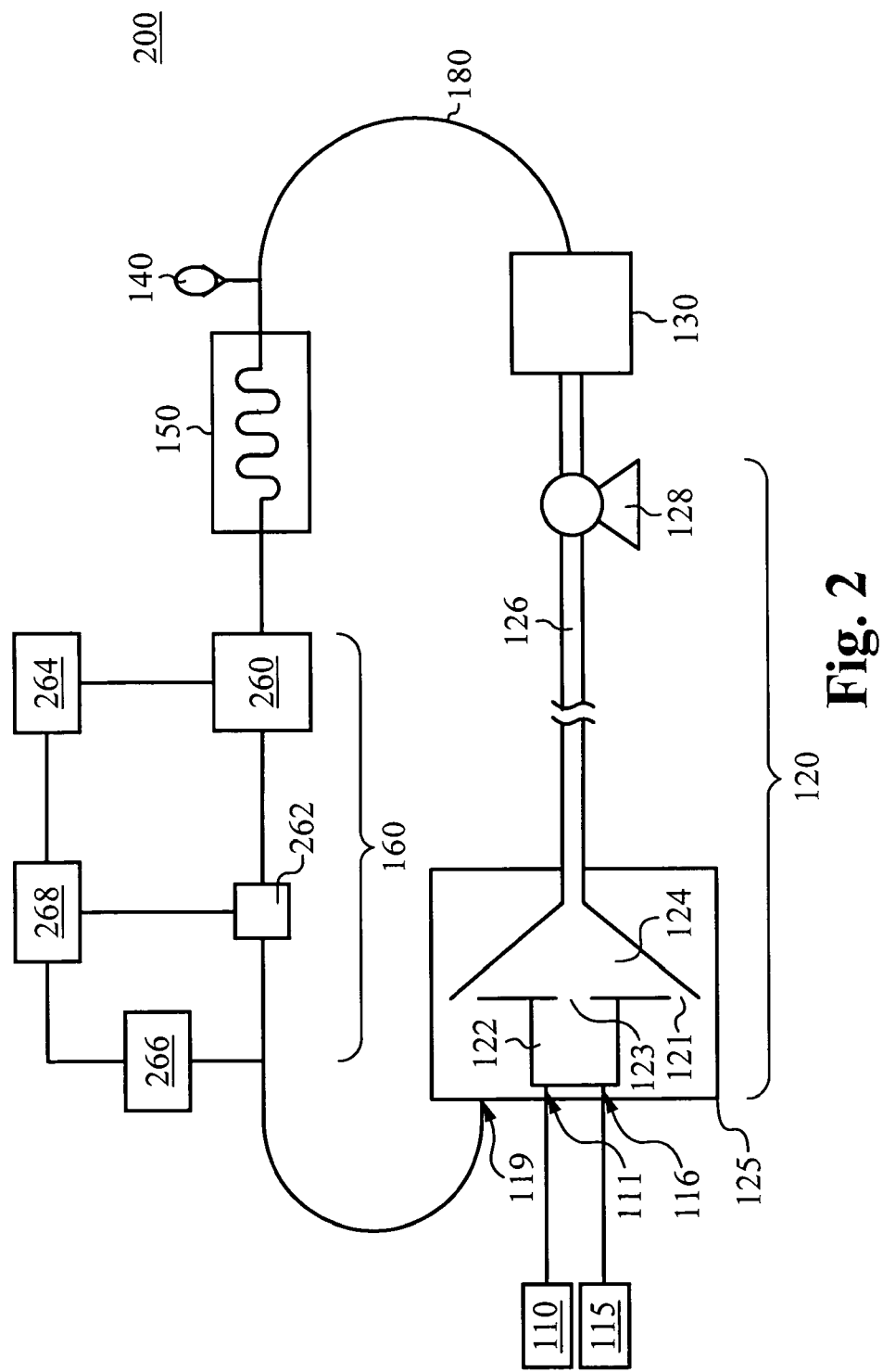
FIG. 2 is a schematic illustration of one embodiment of the particle production system of FIG. 1 with a more detailed embodiment of the content ratio control module in accordance with the principles of the present invention.

FIG. 2 illustrates one embodiment of a particle production system 200, similar to the system 100 of FIG. 1, with a more detailed embodiment of the content ratio control module 160 in accordance with the principles of the present invention. The content ratio control module 160 can include a plurality of components. Some components are fluidly coupled with the conduit system 180. For example, a buffer reservoir 260 is preferably coupled to the conduit system 180 and in fluid communication with the temperature control module 150.

The content ratio control module 140 of some embodiments receives the temperature-controlled, filtered output from the temperature control module 150 in the buffer reservoir 260. The buffer reservoir 260 acts as a fluid buffer, holding the temperature-controlled, filtered output for a period of time before releasing it. During the time while the temperature-controlled, filtered output is within the buffer reservoir 260, the fluid within the output begins to separate based on density because of gravity. In the embodiments where the output comprises a primary fluid and a secondary fluid, the secondary fluid is preferably a less dense fluid. Thus, in these embodiments, the primary fluid concentrates in a lower portion of the buffer reservoir 260, while the secondary fluid concentrates in an upper portion of the buffer reservoir 260.

In a preferred embodiment, the content control module also comprises a content ratio sensor 262 coupled into the conduit system and in fluid communication with the buffer reservoir 260. The content ratio sensor 262 is configured to receive a portion of the fluid mixture, determine the content ratio of the mixture (e.g., the ratio of primary fluid to secondary fluid), and provide one or more signals representing the content ratio.

The buffer reservoir 260 can be configured to permit venting of the secondary fluid from the system 200. In one embodiment of such a configuration, the buffer reservoir 260 is fluidly coupled to a secondary fluid relief element 264. The secondary fluid relief element 264 is in fluid communication with the ambient environment of the particle production system 200 and is configured to selectively permit fluid communication between the buffer reservoir 260 and the ambient atmosphere.

A secondary fluid supply 266 can be fluidly coupled to the conduit system 180 to permit selective fluid communication with the conduit system 180, and thereby with the content ratio sensor 262. The secondary fluid supply 266 is configured to store and selectively introduce an amount of secondary fluid into the fluid mixture to increase the amount of secondary fluid in the mixture relative to the amount of primary fluid, thereby adjusting the content ratio.

The content ratio control module 160 preferably includes a micro-controller 268. The micro-controller 268 is communicatively connected to the content ratio sensor 262, thereby enabling the micro-controller 268 to receive signals from the content ratio sensor 262 that represent the content ratio of the fluid within the conduit system 180 that is in the vicinity of the content ratio sensor 262. The micro-controller 268 is also communicatively connected to the secondary fluid supply 266 and the secondary fluid relief element 264, thereby enabling the micro-controller 268 to select whether the secondary fluid supply 266 is in fluid communication with the conduit system 180 to add secondary fluid and select whether the relief element 264 provides fluid communication between the buffer reservoir 260 and the ambient environment to vent the secondary fluid. The micro-controller 268 can make any or all of these selections based on the content ratio as represented by the signal provided by the content ratio sensor 262.

During the time while the temperature-controlled, filtered output is within the buffer reservoir 260, the secondary fluid relief module 264 can operate to make an initial adjustment to the level of secondary fluid within the buffer reservoir 260. The relief module 264 is preferably coupled to the upper portion of the buffer reservoir 260 to take advantage of the gravity-based separation of the secondary and primary fluids. The micro-controller 268 controls relief of the secondary fluid by the relief module 264. Preferably, the secondary fluid relief module 264 operates by relieving fluid at a continuous rate. The rate can be variable and is preferably determined by the micro-controller 268.

Following the initial adjustment of the secondary fluid level, the adjusted output moves out of the buffer reservoir 260 and into a portion of the conduit system 180 that fluidly couples the buffer reservoir 260 to the content ratio sensor 262. The content ratio sensor 262 detects the ratio of the primary fluid to the secondary fluid within the adjusted output, then sends a signal representing the ratio to the micro-controller 268.

Meanwhile, the adjusted output moves through another portion of the conduit system 180 that fluidly couples the sensor 262 to the outlet of the secondary fluid supply 266. The micro-controller 268 controls the secondary fluid supply 266 to introduce secondary fluid into the adjusted output. The micro-controller 268 uses the signal from the content ratio sensor 262 in determining the rate at which secondary fluid is introduced into the output. The result of these adjustments is the production of a content-controlled, temperature-controlled, filtered output.

This output is channeled through a portion of the conduit system 180 that fluidly couples the outlet of the secondary fluid supply 266 to the conditioning fluid inlet 119 of the particle production core 120. Thus, the content-controlled, temperature-controlled, filtered output is supplied to the particle production core 120 as conditioning fluid.

Because the working gas from the working gas supply 110 becomes part of the output of the particle production core 120, the recirculated conditioning fluid comprises the working gas. In some embodiments, the conditioning fluid is initially supplied from the working gas supply 110 in a charging step, where no precursor material is introduced into the reactor 122. The fluid recirculation system works during the charging step to modulate the characteristics of the conditioning fluid until desired characteristics are reached, at which point, the precursor material is introduced into the reactor 122.

Figure 3A:
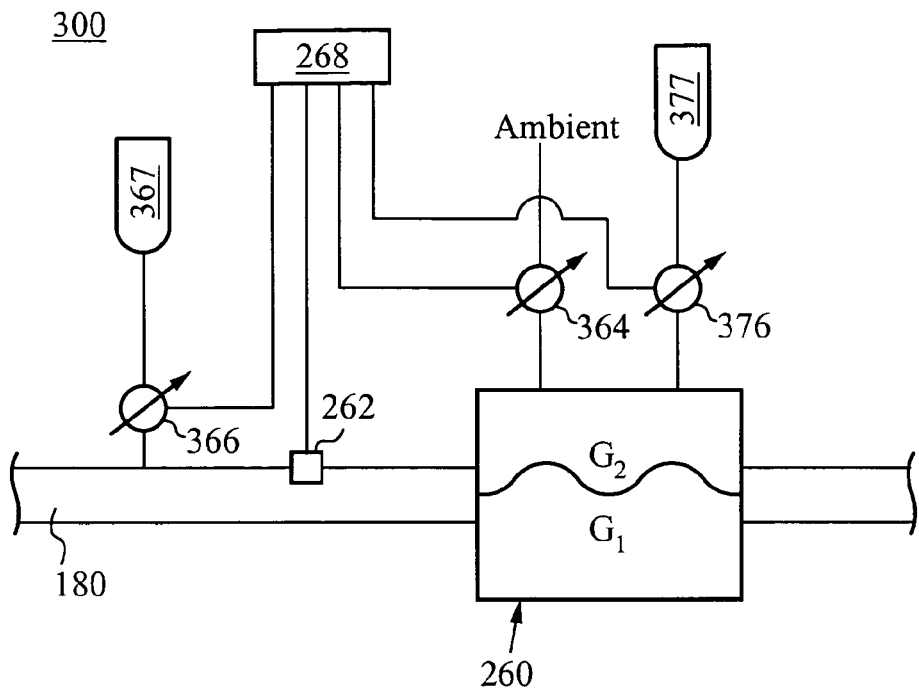
FIG. 3A is a schematic illustration of one embodiment of a content ratio control module in accordance with the principles of the present invention.

FIG. 3A is a schematic illustration of one embodiment of a content ratio control module 300, similar to content ratio control module 160 shown in FIG. 2, in accordance with the principles of the present invention. A portion of the content ratio control module 300 is disposed along the conduit system 180. The conduit system 180 provides fluid communication between a buffer reservoir 260, a content ratio sensor 262, and a secondary fluid supply valve 366.

The secondary fluid supply valve 366 is fluidly coupled to a secondary fluid reservoir 367. The secondary fluid supply reservoir 367 contains a secondary fluid G2. The supply valve 366 enables selective fluid communication between the secondary fluid reservoir 367 and the conduit system 180, thereby allowing for the introduction of additional secondary fluid G2 into the conduit system 180 when appropriate.

Similarly, a primary fluid supply valve 376 is fluidly coupled between the buffer reservoir 260 and a primary fluid reservoir 377, which contains a primary fluid G1, thereby enabling selective fluid communication between the primary fluid reservoir 377 and the buffer reservoir 260 and allowing for the introduction of additional primary fluid G1 into the conduit system 180 when appropriate.

Additionally, the buffer reservoir 260 can be fluidly coupled to a secondary fluid relief valve 364, which is fluidly coupled with the ambient atmosphere, thereby enabling selective fluid communication between the buffer reservoir 260 and the ambient atmosphere. In an exemplary embodiment, the buffer reservoir 260 contains both primary fluid G1 and secondary fluid G2.

The content ratio control module 300 further includes micro-controller 268. The micro-controller 268 is communicatively connected to the content ratio sensor 262, thereby enabling the micro-controller 268 to receive signals from the content ratio sensor 262 that represent the content ratio of the fluid within the conduit system 180 that is in the vicinity of the content ratio sensor 262. The micro-controller 268 is also communicatively connected to the secondary fluid supply valve 366, the secondary fluid relief valve 364, and the primary fluid supply valve 376, thereby enabling the micro-controller 268 to select whether the secondary fluid supply reservoir 367 is in fluid communication with the conduit system 180 to add secondary fluid, to select whether the secondary fluid relief valve 364 provides fluid communication between the buffer reservoir 260 and the ambient environment to vent the secondary fluid, and to select whether the primary fluid supply reservoir 377 is in fluid communication with the conduit system 180 to add primary fluid. The micro-controller 268 can make any or all of these selections based on the content ratio as represented by the signal provided by the content ratio sensor 262.

In operation, the content ratio control module 300 receives the temperature-controlled, filtered output in the buffer reservoir 260. The buffer reservoir 260 acts as a fluid buffer, holding the temperature-controlled, filtered output for a period of time before releasing it.

During the time while the temperature-controlled, filtered output is within the buffer reservoir 260, the fluid within the output begins to separate based on density because of gravity.

In the embodiments where the output comprises a primary fluid G1 and a secondary fluid G2, the secondary fluid G2 is preferably a less dense fluid. Thus, in these embodiments, the primary fluid G1 concentrates in a lower portion of the buffer reservoir 260, while the secondary fluid G2 concentrates in an upper portion of the buffer reservoir 260.

Also, during the time while the temperature-controlled, filtered output is within the buffer reservoir 260, the secondary fluid relief valve 364 can operate to make an initial adjustment to the level of secondary fluid G2 within the buffer reservoir 260. The relief valve 364 is preferably coupled to the upper portion of the buffer reservoir 260 to take advantage of the gravity-based separation of the secondary fluid G2 and primary fluid G1. The micro-controller 268 controls relief of the secondary fluid G2 by the relief valve 364. Preferably, the secondary fluid relief valve 364 operates by relieving secondary fluid G2 at a continuous rate. The rate can be variable and is preferably determined by the controller 268.

Additionally, during the time while the temperature-controlled, filtered output is within the buffer reservoir 260, the primary fluid supply valve 376 and reservoir 377 can operate to make an initial adjustment to the level of primary fluid G1 within the buffer reservoir 260. Although not shown, the primary fluid supply valve 376 can be coupled to the lower portion of the buffer reservoir to take advantage of the gravity-based separation of the secondary fluid G2 and primary fluid G1. The micro-controller 268 controls supply of the primary fluid G1 by the valve 376. Preferably, the primary fluid supply valve 376 operates by supplying primary fluid G1 at a continuous rate. The rate can be variable and is preferably determined by the micro-controller 268.

Following the initial adjustment of the secondary fluid level, the adjusted output moves out of the buffer reservoir 260 and into a portion of the conduit system 180 that fluidly couples the buffer reservoir 260 to the content ratio sensor 262. The content ratio sensor 262 detects the ratio of the primary fluid G1 to the secondary fluid G2 within the adjusted output and sends a signal representing the ratio to the micro-controller 268.

Meanwhile, the adjusted output moves through another portion of the conduit system 180 that fluidly couples the sensor 262 to the secondary fluid supply valve 367. The micro-controller 268 controls the secondary fluid supply valve 3672 to selectively introduce secondary fluid G2 into the adjusted output from the secondary fluid reservoir 367. The micro-controller uses the signal from the content ratio sensor 262 in determining the rate at which secondary fluid G2 is introduced into the output. The result of these adjustments is the production of a content-controlled, temperature-controlled, filtered output.

This output is channeled through a portion of the conduit system 180 that fluidly couples the content ratio control module 300 to the conditioning fluid inlet of the particle production core 120. Thus, the content-controlled, temperature-controlled, filtered output is supplied to the particle production core 120 as conditioning fluid.

Figure 3B:
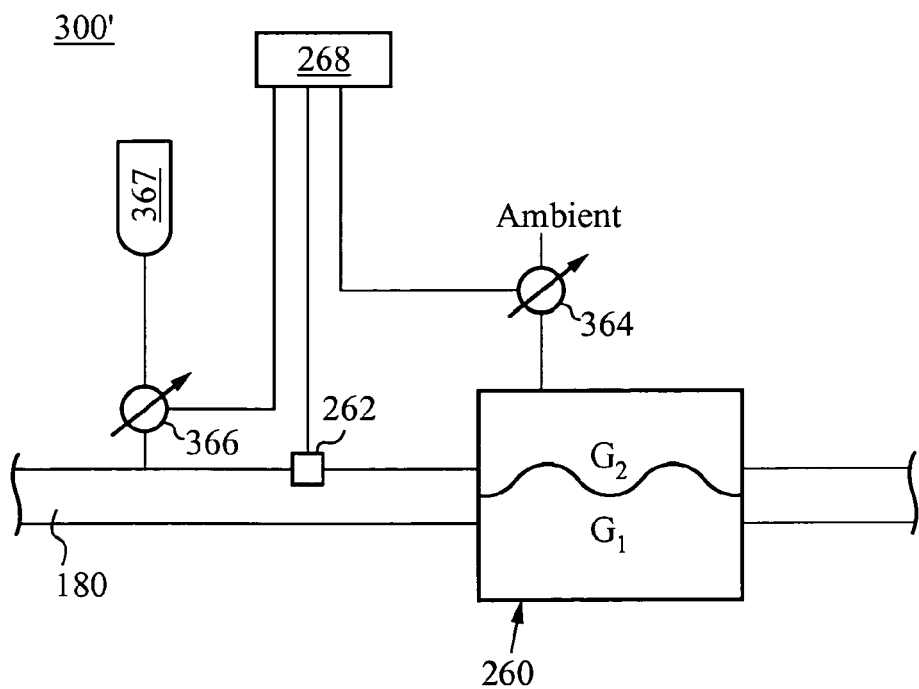
FIG. 3B is a schematic illustration of another embodiment of a content ratio control module in accordance with the principles of the present invention.

FIG. 3B is a schematic illustration of another embodiment of a content ratio control module 300' in accordance with the principles of the present invention. Content ratio control module 300' is the same as content ratio control module 300, except that module 300' does not include primary fluid supply valve 376 or primary fluid supply reservoir 377. In an alternative embodiment, primary fluid supply valve 376 and primary fluid supply reservoir 377 can be present while secondary fluid supply valve 366 or secondary fluid supply reservoir 367 are excluded. It is contemplated that several other different configurations are also well within the scope of the present invention.

Figure 4:
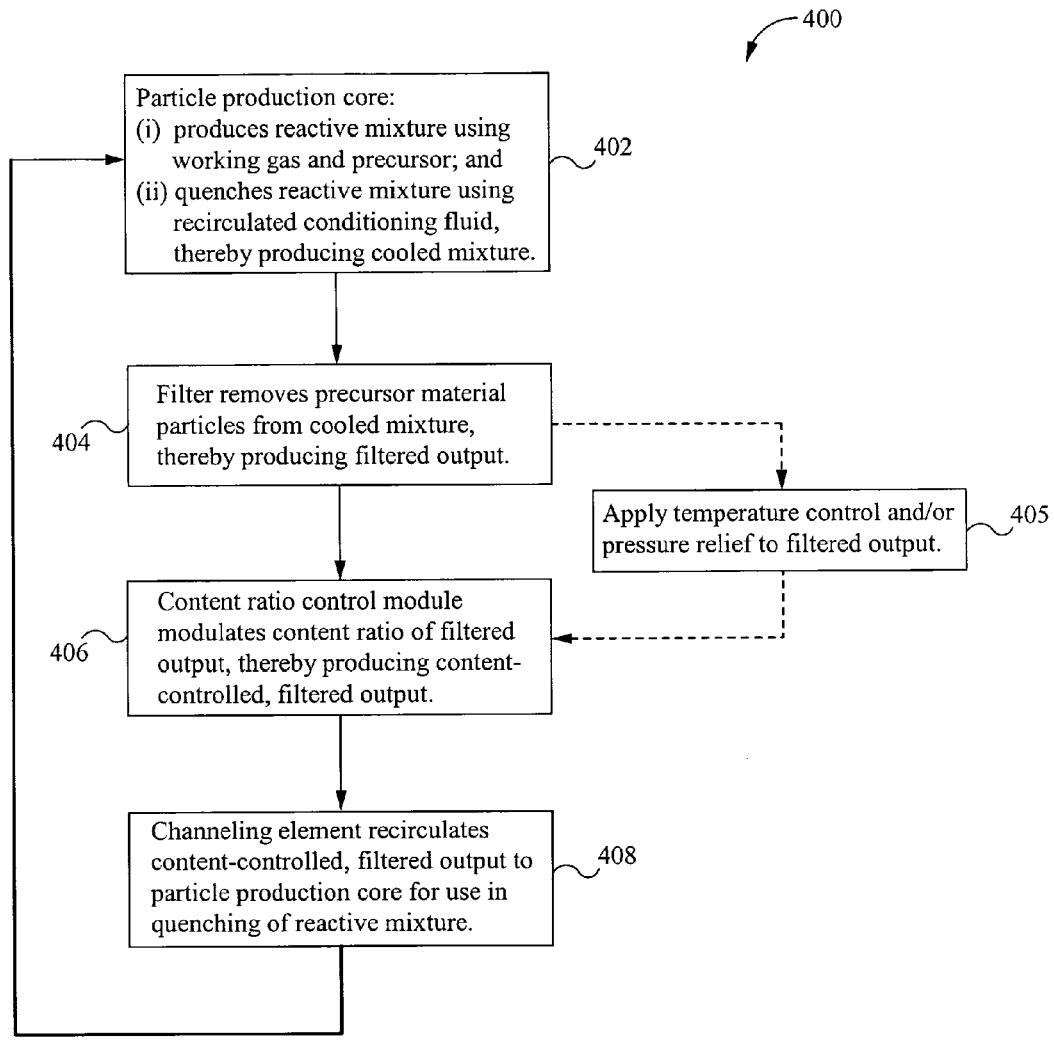
FIG. 4 is a flow chart illustrating one embodiment of a method of recirculating a fluid in a particle production system in accordance with the principles of the present invention.

FIG. 4 is a flow chart illustrating one embodiment of a method of recirculating a fluid in a particle production system in accordance with the principles of the present invention.

At step 402, the particle production core performs two main functions. First, it produces a reactive particle-gas mixture using a working gas and a precursor material. Preferably, this operation is performed via a particle production reactor as discussed above. Second, the particle production core quenches the reactive particle-gas mixture using recirculated conditioning fluid, resulting in the production of a cooled particle-gas mixture, which comprises a plurality of precursor material particles. Preferably, this operation is performed via a quenching chamber as discussed above.

The cooled particle-gas mixture then flows out of the particle production core and into the fluid recirculation system for preparation before being re-introduced back into the particle production core for use in quenching.

At step 404, the cooled particle-gas mixture flows into a filter, where the filter removes the precursor material particles from the cooled particle-gas mixture, thereby producing a filtered output. It is contemplated that, in some embodiments, the filter can be configured to remove all of the precursor material particles in the cooled particle-gas mixture, leaving no precursor material particles in the filtered output, while in other embodiments, the filter can be configured to remove less than all of the precursor material particles in the cooled particle-gas mixture, leaving a certain amount of the precursor material particles remaining in the filtered output.

At this point, the filtered output flows to the content ratio control module. However, it is contemplated that the filtered output can optionally be subjected to additional preparation before reaching the content ratio control module. If this additional preparation is desired, then at step 405, the filtered output can undergo temperature control and/or pressure relief, as discussed above with respect to the temperature module and the pressure relief module. For example, a portion of the filtered output can be vented to ambient, thereby reducing the pressure of the filtered output. The filtered output can then flow through a heat exchanger, thereby reducing its temperature.

At step 406, the filtered (and possibly temperature-controlled and pressure-relieved) output reaches the content ratio control module, where its content ratio is modulated. In a preferred embodiment, the filtered output comprises a distinct primary fluid and a distinct secondary fluid, and the content ratio is the ratio of the primary fluid to the secondary fluid. As discussed above, this modulation of the content ratio can involve one or more operations, including, but not limited to, a decrease in the amount of a certain fluid or the increase in the amount of a certain fluid. These operations are preferably performed with the use of one or more components, such as the micro-controller, sensor, reservoirs, and valves discussed above. The result of this content ratio modulation is the production of a content-controlled, filtered output that is now acceptable for reuse as conditioning fluid in quenching the reactive particle-gas mixture back in the particle production core.

At step 408, a channeling element recirculates the content-controlled, filtered output into the particle production core for use as conditioning fluid in the quenching of the reactive mixture back at step 402. This process 400 can be repeated several times, wherein the same conditioning fluid is recirculated and reused over and over again.

Embodiments of the present invention permit the recirculation and reuse of conditioning fluids within a particle production system. Furthermore, these embodiments permit the adjustment of a content ratio of the conditioning fluids, which may otherwise change undesirably with system use. Particle production systems incorporating embodiments of the present invention do not need a constant supply of fresh conditioning fluid. When fresh fluid is supplied, the system uses it for multiple production runs. Since the cost of fresh conditioning fluid is spread over more than one production run, the unit cost of the particles produced using the present invention is less than with conventional means.

Additionally, some embodiments described herein permit recirculation using filters with a specified tolerance so as not to filter out every particle from the output. These embodiments allow for use of less expensive filters on dedicated production lines where cross-contamination is not an issue.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A particle production system, comprising:
a particle production reactor configured to produce a reactive particle-gas mixture from a precursor material and a working gas;
a quench chamber with a fluid inlet, a reactive mixture inlet fluidly coupled to the particle production reactor, and a cooled mixture outlet, wherein the quench chamber is configured to receive a conditioning fluid at the fluid inlet, to receive the reactive particle-gas mixture from the particle production reactor at the reactive mixture inlet, and to mix the conditioning fluid with the reactive particle-gas mixture to produce a cooled particle-gas mixture, the cooled particle-gas mixture comprising a plurality of precursor material particles and an output fluid, the output fluid including the conditioning fluid;
a filter element fluidly coupled to the cooled mixture outlet and configured to receive and filter the output fluid from the quench chamber to produce a filtered output;
a temperature control module fluidly coupled to the filter element and configured to control the temperature of the filtered output to produce a temperature-controlled, filtered output, wherein the temperature-controlled, filtered output comprises a primary fluid and a secondary fluid;
a content ratio control module fluidly coupled to the temperature control module and configured to modulate a content ratio of the temperature-controlled, filtered output to produce a content-controlled, temperature-controlled, filtered output, wherein the content ratio is the ratio of the primary fluid to the secondary fluid; and
a channeling element fluidly coupling the content ratio control module to the fluid inlet of the quench chamber, and configured to supply the content-controlled, temperature-controlled, filtered output to the fluid inlet of the quench chamber, wherein the content-controlled, temperature-controlled, filtered output is provided to the quench chamber as the conditioning fluid.

2. The system of claim 1, wherein the particle production reactor is configured to energize the working gas to form a plasma, and to apply the plasma to the precursor material to produce the reactive particle-gas mixture.

3. The system of claim 1, further comprising a suction generator configured to generate a suction force at the cooled mixture outlet of the quench chamber to draw the output fluid from the quench chamber.

4. The system of claim 1, wherein the filter element is configured to remove precursor material particles from the cooled particle-gas mixture to produce the filtered output including the output fluid.

5. The system of claim 4, wherein the filter element comprises a high efficiency particulate air (HEPA) filter.

6. The system of claim 1, further comprising a pressure relief module fluidly coupled between the filter element and the temperature control module, wherein the pressure relief module is configured to reduce the pressure of the filtered output if the pressure exceeds a predetermined threshold.

7. The system of claim 1, wherein the temperature control module comprises a heat exchanger.

8. The system of claim 1, wherein the content ratio control module comprises:
   a sensor configured to measure the content ratio of the temperature-controlled, filtered output, and to produce a signal representing the measured content ratio; and
   a controller communicatively connected to the sensor and configured to receive the signal from the sensor and control the modulation of the content ratio of the temperature-controlled, filtered output based on the received signal.

9. The system of claim 8, wherein the content ratio control module further comprises a buffer reservoir fluidly coupled between the temperature control module and the sensor, wherein the buffer reservoir is configured to receive the temperature-controlled, filtered output from the temperature control module and to store the temperature-controlled, filtered output before the content ratio of the temperature-controlled, filtered output is modulated.

10. The system of claim 9, wherein the content ratio control module further comprises a fluid relief valve communicatively connected to the controller and fluidly coupled between the buffer reservoir and the ambient atmosphere, wherein the fluid relief valve is configured to vent the secondary fluid from the buffer reservoir to the ambient atmosphere in response to a signal from the controller.

11. The system of claim 9, wherein the content ratio control module further comprises:
   a secondary fluid supply valve communicatively connected to the controller and configured to add secondary fluid from a secondary fluid supply reservoir to the measured temperature-controlled, filtered output in response to a signal from the controller to produce the content-controlled, temperature-controlled, filtered output.

12. The system of claim 11, wherein the content ratio control module further comprises:
   a primary fluid supply valve communicatively connected to the controller and configured to add primary fluid from a primary fluid supply reservoir into the stored temperature-controlled, filtered output in the buffer reservoir in response to a signal from the controller.

13. A particle production system comprising:
   a particle production reactor configured to produce a reactive particle-gas mixture from a precursor material and a working gas;
   a quench chamber with a fluid inlet, a reactive mixture inlet fluidly coupled to the particle production reactor, and a cooled mixture outlet, wherein the quench chamber is configured to receive a conditioning fluid at the fluid inlet, to receive the reactive particle-gas mixture from the particle production reactor at the reactive mixture inlet, and to mix the conditioning fluid with the reactive particle-gas mixture to produce a cooled particle-gas mixture, the cooled particle-gas mixture comprising a plurality of precursor material particles and an output fluid, the output fluid including the conditioning fluid;
   a filter element fluidly coupled to the cooled mixture outlet and configured to receive and filter the output fluid from the quench chamber to produce a filtered output;
   a temperature control module fluidly coupled to the filter element and configured to control the temperature of the filtered output to produce a temperature-controlled, filtered output, wherein the temperature-controlled, filtered output comprises a primary fluid and a secondary fluid;
   a buffer reservoir fluidly coupled to the temperature control module, wherein the buffer reservoir is configured to receive the temperature-controlled, filtered output from the temperature control module and to store the temperature-controlled, filtered output;
   a sensor fluidly coupled to the buffer reservoir and configured to measure a content ratio of the stored temperature-controlled, filtered output, and to produce a signal representing the measured content ratio, wherein the content ratio is the ratio of the primary fluid to the secondary fluid;
   a controller communicatively connected to the sensor and configured to receive the signal from the sensor and control the modulation of the content ratio of the measured temperature- controlled, filtered output based on the received signal;
   a fluid relief valve communicatively connected to the controller and fluidly coupled between the buffer reservoir and the ambient atmosphere, wherein the fluid relief valve is configured to vent the secondary fluid from the buffer reservoir to the ambient atmosphere in response to a signal from the controller;
   a secondary fluid supply valve communicatively connected to the controller and configured to add secondary fluid from a secondary fluid supply reservoir to the measured temperature- controlled, filtered output in response to a signal from the controller to produce a content-controlled, temperature-controlled, filtered output; and
   a channeling element fluidly coupling the sensor to the fluid inlet of the quench chamber, and configured to supply the content-controlled, temperature-controlled, filtered output to the fluid inlet of the quench chamber, wherein the content-controlled, temperature-controlled, filtered output is provided to the quench chamber as the conditioning fluid.

14. The system of claim 13, wherein the particle production reactor is configured to energize the working gas to form a plasma, and to apply the plasma to the precursor material to produce the reactive particle-gas mixture.

15. The system of claim 13, further comprising a suction generator configured to generate a suction force at the cooled mixture outlet of the quench chamber to draw the output fluid from the quench chamber.

16. The system of claim 13, wherein the filter element is configured to remove precursor material particles from the cooled particle-gas mixture to produce the filtered output including the output fluid.

17. The system of claim 16, wherein the filter element comprises a high efficiency particulate air (HEPA) filter.

18. The system of claim 13, further comprising a pressure relief module fluidly coupled between the filter element and the temperature control module, wherein the pressure relief module is configured to reduce the pressure of the filtered output if the pressure exceeds a predetermined threshold.

19. The system of claim 13, wherein the temperature control module comprises a heat exchanger.

20. The system of claim 13, further comprising a primary supply valve communicatively connected to the controller and configured to add primary fluid from a primary fluid supply reservoir into the stored temperature-controlled, filtered output in the buffer reservoir in response to a signal from the controller.

* * * * *

UNITED STATES PATENT AND TRADEMARK OFFICE
CERTIFICATE OF CORRECTION

| | | |
|---|---|---|
| PATENT NO. | : 8,906,316 B2 | Page 1 of 1 |
| APPLICATION NO. | : 13/907667 | |
| DATED | : December 9, 2014 | |
| INVENTOR(S) | : Frederick P. Layman | |

It is certified that error appears in the above-identified patent and that said Letters Patent is hereby corrected as shown below:

ON THE TITLE PAGE:

In Column 1, in item (63) of Related U.S. Application Data:

Please delete "(63) Continuation of application No. 12/151,765, filed on May 8, 2008, now Pat. No. 8,574,408." and insert --(62) Division of application No. 12/151,765, filed on May 8, 2008, now Pat. No. 8,574,408.--

Signed and Sealed this
Eighth Day of March, 2016

Michelle K. Lee
*Director of the United States Patent and Trademark Office*